United States Patent
Bruce et al.

(10) Patent No.: US 7,056,577 B1
(45) Date of Patent: *Jun. 6, 2006

(54) BODY FOR PROVIDING INGROWTH AND GROWTH OF BONE TISSUE AND/OR CONNECTIVE TISSUE AND METHOD OF MAKING SUCH A BODY

(75) Inventors: Ingrid Bruce, Viken (SE); Lars Bruce, Viken (SE)

(73) Assignee: Tigran Technologies AB, Helsingborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,439

(22) PCT Filed: Apr. 28, 2000

(86) PCT No.: PCT/SE00/00802

§ 371 (c)(1),
(2), (4) Date: Dec. 3, 2001

(87) PCT Pub. No.: WO00/64504

PCT Pub. Date: Nov. 2, 2000

(30) Foreign Application Priority Data

Apr. 28, 1999 (SE) .................................. 9901523

(51) Int. Cl.
  *B32B 3/26* (2006.01)
  *A61F 2/28* (2006.01)
(52) U.S. Cl. .............................. 428/312.8; 428/315.5; 428/315.7; 428/305.5; 428/131; 623/23.63; 623/23.52; 623/16.11; 164/119

(58) Field of Classification Search ............. 428/304.4, 428/306.6, 307.3, 131, 312.2, 312.8, 315.7; 623/16.11, 17.11, 11.11, 23.52, 23.63; 164/119
See application file for complete search history.

(56) References Cited

U.S. PATENT DOCUMENTS 4,154,675 A * 5/1979 Jowett et al. ............... 210/675

(Continued)

FOREIGN PATENT DOCUMENTS

EP 0 159 036 10/1985

(Continued)

OTHER PUBLICATIONS

Swedish and English language Abstract for SE 9803078-6 filed Sep. 9, 1998 (corresponding to PC Publ. No. WO 00/13615).

*Primary Examiner*—Hai Vo
(74) *Attorney, Agent, or Firm*—Smith Gambrell & Russell LLP

(57) ABSTRACT

A body, such as a grain, for providing ingrowth and growth of bone tissue and/or connective tissue. The body consists of a plastic or non-essentially elastic biocompatible material, preferably metal or metal alloy. It is also porous, having the following porosity characteristics: (a) the porosity is continuous and (b) the opening of cavities/indentations/pockets and the ducts connecting them has the width of >about 50 µm for bone tissue and >about 10 µm for connective tissue. In a method of making such a body, the body has been produced by blowing gas into a melt of metal. An advantageous use of bodies according to the invention is enclosing thereof in a casing, formed with openings, for making an implant, such as a spinal implant.

18 Claims, 3 Drawing Sheets

U.S. PATENT DOCUMENTS

Figure 1:
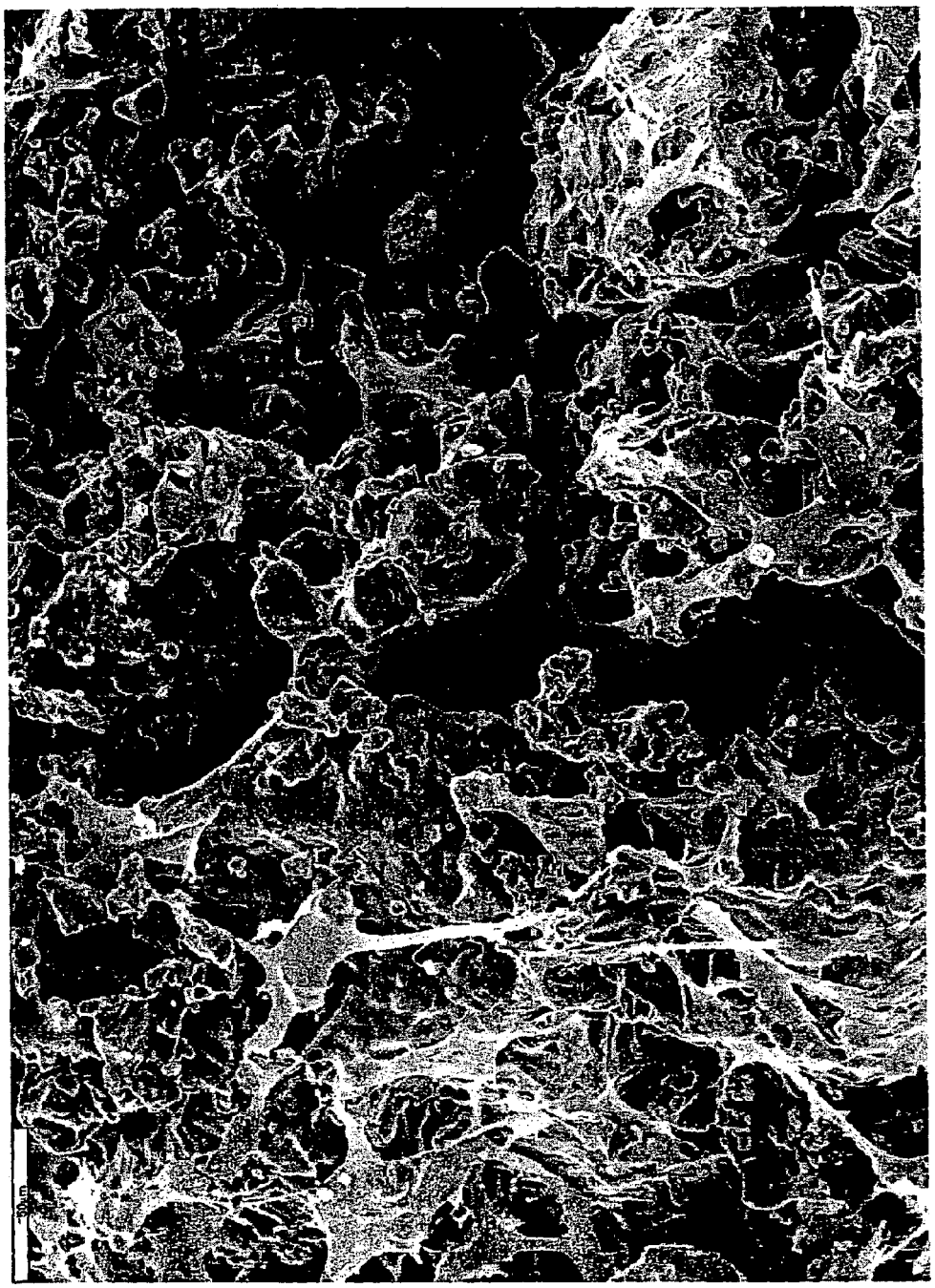

| | | | | |
|---|---|---|---|---|
| 4,318,990 | A | * 3/1982 | Thomson et al. | 435/219 |
| 4,713,076 | A | 12/1987 | Draenert | 623/16 |
| 5,015,247 | A | 5/1991 | Michelson | 606/61 |
| 5,015,256 | A | 5/1991 | Bruce et al. | 623/18 |
| 5,217,496 | A | 6/1993 | Bruce et al. | 623/16 |
| 5,282,861 | A * | 2/1994 | Kaplan | 623/23.51 |
| 5,464,440 | A | 11/1995 | Johansson | 623/16 |
| 5,645,598 | A | 7/1997 | Brosnahan, II | 623/17 |
| 5,676,700 | A | 10/1997 | Black et al. | 623/16 |
| 5,766,253 | A | 6/1998 | Brosnahan, III | 623/17 |
| 5,986,169 | A | 11/1999 | Gjunter | 623/16 |
| 6,565,606 | B1 | 5/2003 | Bruce et al. | 623/23.63 |
| 6,599,620 | B1 * | 7/2003 | Fujita et al. | 428/317.9 |

FOREIGN PATENT DOCUMENTS

| | | |
|---|---|---|
| EP | 0 267 624 | 5/1988 |
| EP | 0 856 299 | 8/1998 |
| SE | 462 638 | 8/1990 |
| SE | 515572 | 9/1998 |
| WO | WO 93/13815 | 7/1993 |
| WO | WO 97/24084 | 10/1997 |
| WO | WO 9816267 | 4/1998 |
| WO | WO 9830620 A1 * | 7/1998 |
| WO | WO 99/13478 | 3/1999 |
| WO | WO 99/34845 | 7/1999 |
| WO | WO 00/13615 | 3/2000 |

* cited by examiner

BODY FOR PROVIDING INGROWTH AND GROWTH OF BONE TISSUE AND/OR CONNECTIVE TISSUE AND METHOD OF MAKING SUCH A BODY

SE-B-462,638 discloses a means for fixing an elongate prosthesis, such as the stem of a femoral prosthesis, to living tissue which defines a cavity in which a length of the prosthesis is received with a gap to the boundary of the cavity. Essentially the entire gap is filled with loose, but packed grains of a biocompatible material, said grains interlocking. As an example of granular material titanium is mentioned, and the grains are stated to be irregular, essentially non-elastic and preferably porous, the latter property being said to bind growth of bone tissue which has grown from the osseous wall. The porosity has been obtained by blowing gas through a melt of the granular material.

U.S. Pat. No. 5,217,496 discloses an implant suited for use in living bone tissue and comprising a support of titanium having a porous outer surface and an attached layer of a mixture consisting of disintegrated living bone tissue and titanium powder. The mixture is supplied with nutriment which makes the disintegrated bone tissue grow and form tissue which connects the disintegrated bone tissue and the titanium powder with each other and with the support.

U.S. Pat. No. 5,676,700 discloses biocompatible structure elements for repair, reinforcement and replacement of bone tissue, said elements being indicated to form an osteoconductive or osteoinductive matrix in a bone tissue cavity. The material of the elements can be titanium and the elements are said advantageously to be microporous for ingrowth of natural bone.

All the documents above mention as biocompatible material, in addition to titanium, inter alia, hydroxylapatite, bioceramics, bioglass.

In the above documents, porosity of biocompatible materials is thus pointed out to cause something favourable for binding of bone tissue.

According to the invention, it has surprisingly been found that a predetermined measure of the porosity of biocompatible material is in fact a decisive factor as regards the growth rate of bone tissue. It has been found that while surface porosity certainly allows binding of bone tissue, a significantly increased growth rate of bone tissue and a larger amount of bone are obtained and, thus, a significantly improved anchoring and strength of bone tissue on the biocompatible material if the body, such as a grain, of the biocompatible material is continuously porous, the porosity of the body has a minimum limit value.

An additional advantage of the invention is obtained by the strength of the porous granule with grown-in bone tissue being greater than if bone is not allowed to grow in. Owing to the ingrowth of bone, the strength will mainly be carried by the bone tissue, which is favourable from the biomechanical point of view.

By "continuously porous" is here meant a porosity which allows bone tissue to grow through the porous body, such as the grain of biocompatible material. According to the invention, such porosity results in cavities in the body which are interconnected by ducts, passages, so that growth of bone tissue onto a part of the outer surface of the body allows the growth to continue through the body and out through other parts of the outer surface of the body. By cavity is meant indentations, pits, pockets of an arbitrary shape, and the ducts, passages, interconnecting these cavities can have an arbitrary form and constitute part of the cavities. Examples of such a structure can be found in nature in corals or dripstone caves.

By minimum limit value is here meant an opening of an indentation, pit, pocket and a duct opening having a width of >about 50 µm. A smaller opening dimension restricts or inhibits the growth of bone tissue, probably because the supply of nutriment is inhibited and the bone is prevented from developing its normal structure with the elements that are included. In fact there is no upper limit of the porosity of the body. The upper limit is rather determined by the strength properties of the body.

According to the invention, cavities can be allowed to form of surface pores in bodies which are located next to each other and have open surface pores, so that the surface pores in one body form a cavity or duct/passage with the surface pores in the other body.

According to the invention, it has also been found that a brittle biocompatible material, such as hydroxylapatite, is not optimal for the purposes of the invention when such material is used for repair, reinforcement and replacement of natural bone. Such a material easily decomposes when subjected to a load, which inevitably occurs, for example when the human body or a part of the human body, in which the biocompatible body, such as the grain, is located, is subjected to a load when e.g. the extremities move. Decomposed parts of a body of biocompatible material cause an unfavourable inflammatory reaction which inhibits the formation of bone and which often results in bone resorption.

According to the invention, a metallic material or non-brittle composites are therefore chosen, where natural material, such as hydroxylapatite, bioceramics etc., can be included as a component in the material of the porous body and another component, such as plastic, guarantees plasticity. The body material according to the invention should in fact be plastic or non-essentially elastic. Excessive elasticity causes pressure on the bone tissue, with the ensuing destruction thereof.

Titanium (titanium dioxide) is advantageously selected as metallic material. The porosity of the titanium body is advantageously achieved by blowing gas through a melt of titanium. This makes it possible to produce titanium grains, as mentioned in SE-B-462,638.

The requirement as to porosity as stated above is, however, not automatically satisfied by blowing gas through a melt of metal. According to the invention, a quality check is therefore made of the porosity of the grains obtained in this manner to ensure that they satisfy the requirement. The quality check can be carried out, for example, by means of fluoroscopy at a suitable wavelength and a TV receiver and automatic separation (e.g., from a conveyor belt) of grains that do not satisfy the above-mentioned requirement.

The above limit value of greater than about 50 µm relates to grain porosity sizing relative to the ingrowth of bone tissue. If ingrowth of connective tissue is desired instead of or at the expense of bone tissue, the limit value is instead greater than about 50–10 µm.

A porous body, such as a grain, according to the invention can be implanted in a living body, such as a human body, for filling a bone cavity, as replacement, after growth of bone tissue in vivo, a lost leg (rheumatism, osteoporosis) or for fixing a prosthesis according to SE-B-462,638. A porous body according to the invention can also serve as a base for preculturing of bone tissue in vitro or be filled with a nutrient solution containing, inter alia, growth factors in vitro for subsequent implanting in living tissue. In the case of filling a bone cavity, it is preferred for the body to be granular and irregular and to have the size less than 10 mm, so that a plurality of grains optimally fill the bone cavity.

The porous body can be filled with a decomposable material, for example of a so-called matrix of the natural material. Examples of such natural matrices are gels of collagen, fibrin, starch and hyaluronic acid. According to the invention, this matrix is decomposed to be replaced with the ingrowing bone tissue. The ingrowth of bone tissue can be further stimulated if growth-stimulating substances are added to the decomposable material, above all growth factors such as TGF beta (Transforming Growth Factor beta) or BGF (Bone Growth Factor). The pores in the body according to the invention can be moved with the gel material, e.g. by suction, before the material is ready-gelled.

Smaller bodies, grains according to the invention can be enclosed in a casing, flexible or rigid, for producing an implant. For example, grains according to the invention can be enclosed in a rigid sleeve so as to form, together with the sleeve, a spinal implant, see e.g. the sleeve in U.S. Pat. No. 5,015,247. Other possibilities of enclosing in a casing are disclosed in SE 9803078-6. The casing has openings to allow ingrowth and growth of biological cell material to and from the grains, through the casing. Grains according to the invention can be mixed with decomposed biological tissue.

Figure 2:
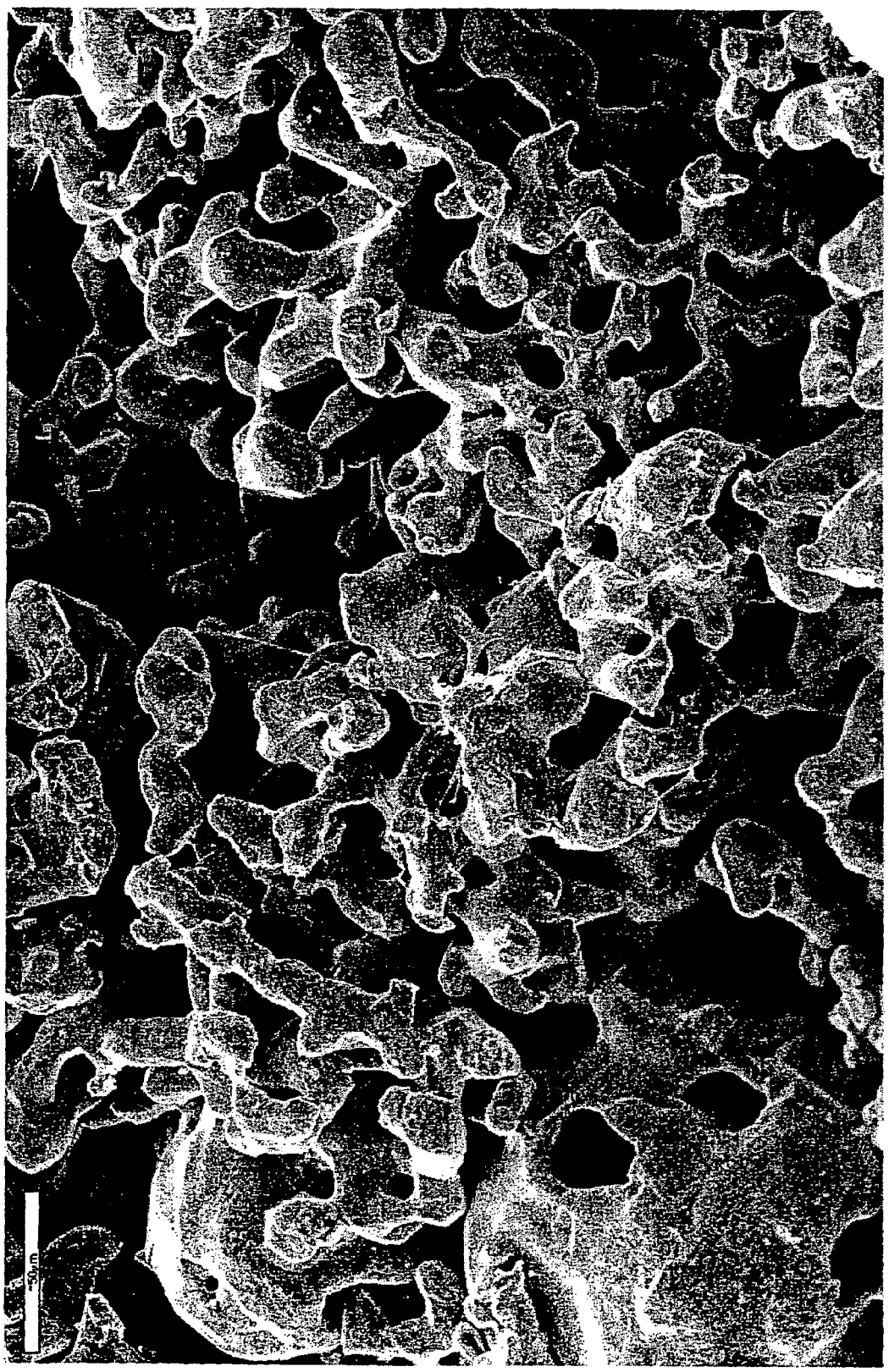

Embodiments of the invention are illustrated in the accompanying Figures which are electron microscope images and of which FIG. 1 shows a porous structure according to the invention and FIG. 2 shows another porous structure according to the invention of the outer surface of a titanium grain.

Figure 3:

FIG. 3 is an image of a thin section of a titanium grain with porosity according to the invention.

All images are made of an irregular grain or granule which has been removed from the femur in a human body after implanting using a vibration technique which is described in more detail in SE-B-462,638.

FIG. 1 shows a structure in the form of a mound of stones and FIG. 2 shows a coral structure. The structures have been provided by blowing gas through a melt of titanium and applying the above-mentioned quality check. Both images show a whitish-grey film of living material, the prestage of bone tissue, which covers the outer surface of the grain and has penetrated into the cavities and gaps in the pores of the monolithic titanium grain. FIG. 1 also shows bone cell growths bridging cavities/gaps in the structure.

FIG. 3 illustrates bone tissue which has intersected, penetrated a grain according to the invention.

Clinical analyses have proved that the bone tissue in grains according to FIGS. 1–3 had a composition of 95–98% bone, 2% marrow and 0–3% connective tissue, which essentially corresponds to the composition of the bone outside the grains in their vicinity.

The invention claimed is:

1. An irregularly shaped implant grain for providing ingrowth and growth of bone tissue and/or connective tissue, and said implant grain being made of a plastic or essentially non-elastic biocompatible implant material, wherein said grain includes multiple pores that are continuous through said grain, and openings of said multiple pores and ducts or passages interconnecting at least a portion of said multiple pores have a width of greater than about 50 μm, and wherein said grain is made of a metal or metal alloy.

2. The grain as claimed in claim 1, wherein said grain is made of titanium.

3. The grain as claimed in claim 1, wherein said grain size is less than 10 mm.

4. An aggregate of grains which includes grains as claimed in claim 1.

5. An aggregate of grains for providing ingrowth and growth of bone tissue, connective tissue or both, which aggregate consists essentially of grains according to the grain of claim 1.

6. The aggregate of claim 5, wherein said aggregate of grains is configured for implant use.

7. The grain of claim 1 wherein said multiple pores of said grain are randomly distributed.

8. The grain of claim 1 wherein the multiple pores that are continuous are sized to allow bone tissue to grow through said grain.

9. The grain of claim 1 wherein said grain is of a monolithic structure with said multiple pores extending into the surface of that monolithic structure.

10. An irregularly shaped grain for providing ingrowth and growth of bone tissue and/or connective tissue, said grain being made of a plastic or essentially non-elastic biocompatible material, wherein said grain includes multiple pores that are continuous through said grain, and openings of said multiple pores and ducts or passages interconnecting at least a portion of said multiple pores have a width of greater than about 50 μm, wherein said multiple pores are filled with a decomposable material, and wherein said grain is made of a metal or metal alloy.

11. The grain as claimed in claim 10, wherein the decomposable material contains growth-stimulating substances.

12. The grain as claimed in claim 10, wherein said decomposable material includes a matrix of natural material.

13. The grain as claimed in claim 12, wherein said matrix of natural material includes a gel of at least one of collagen, fibrin, starch, and hyaluronic acid.

14. An irregularly shaped grain for providing ingrowth and growth of bone tissue and/or connective tissue, said grain being made of a plastic or essentially non-elastic biocompatible material, wherein said grain includes multiple pores that are continuous through said grain, and openings of said multiple pores and ducts or passages interconnecting at least a portion of said multiple pores have a width of greater than about 50 μm, wherein said grain has a coral structure, and wherein said grain is made of a metal or metal alloy.

15. An irregularly shaped grain for providing ingrowth and growth of bone tissue and/or connective tissue, said grain being made of a plastic or essentially non-elastic biocompatible material, wherein said grain includes multiple pores that are continuous through said grain, and openings of said multiple pores and ducts or passages interconnecting at least a portion of said multiple pores have a width of greater than about 50 μm, and wherein said grain is made of a metal or metal alloy.

16. An implant comprising a plurality of grains and a casing, said grains being grains that are irregularly shaped grains for providing ingrowth and growth of bone tissue and/or connective tissue, said grains being made of a plastic or essentially non-elastic biocompatible material, wherein said grains include multiple pores that are continuous through the grain, and openings of said multiple pores and ducts or passages interconnecting at least a portion of said multiple pores have a width of greater than about 50 μm, and wherein said grain is made of a metal or metal alloy.

17. The implant as claimed in claim 16, wherein the casing is a rigid cylindrical sleeve for producing a spinal implant.

18. A method for making a metal or metal alloy grain, which is an irregularly shaped grain for providing ingrowth and growth of bone tissue and/or connective tissue, said metal or metal alloy grain being made of a plastic or essentially non-elastic biocompatible material, wherein said grain includes multiple pores that are continuous through said grain, and openings of said multiple pores and ducts or passages interconnecting at least a portion of said multiple pores have a width of greater than about 50 μm, comprising blowing gas through a melt of a metal or metal alloy to produce multiple grains, and separating grains having multiple pore openings, which pore openings have a width of greater than 50 μm, and ducts or passages, connecting at least a portion of said multiple pore openings, having a width of greater than 50 μm.

\* \* \* \* \*